US008420602B2

(12) United States Patent
Miller

(10) Patent No.: US 8,420,602 B2
(45) Date of Patent: Apr. 16, 2013

(54) ENDOCANNABINOID CONJUGATE AND A PHARMACEUTICAL COMPOSITION FOR TREATMENT OF NEURONAL DISORDERS

(76) Inventor: Landon C. G. Miller, Tuscaloosa, AL (US)

( * ) Notice: Subject to any disclaimer, the term of this patent is extended or adjusted under 35 U.S.C. 154(b) by 559 days.

(21) Appl. No.: 11/129,526

(22) Filed: May 13, 2005

(65) Prior Publication Data

US 2006/0058222 A1 Mar. 16, 2006

Related U.S. Application Data

(63) Continuation-in-part of application No. 11/023,196, filed on Dec. 27, 2004, now Pat. No. 7,074,775, and a continuation-in-part of application No. 11/023,241, filed on Dec. 27, 2004, now Pat. No. 7,884,079, and a continuation-in-part of application No. 11/023,240, filed on Dec. 27, 2004, now Pat. No. 7,151,084, and a continuation-in-part of application No. 11/023,309, filed on Dec. 27, 2004, now Pat. No. 7,157, 421.

(60) Provisional application No. 60/609,659, filed on Sep. 14, 2004.

(51) Int. Cl.
*A61K 38/00* (2006.01)

(52) U.S. Cl.
USPC .......................................... 514/18.4; 530/302

(58) Field of Classification Search ........................ None
See application file for complete search history.

(56) References Cited

U.S. PATENT DOCUMENTS

| | | | | |
|---|---|---|---|---|
| 4,145,347 | A | 3/1979 | L'Italien et al. | 546/208 |
| 4,311,640 | A * | 1/1982 | Kuroda et al. | 530/332 |
| 4,355,027 | A | 10/1982 | Growdon et al. | 424/199 |
| 4,362,716 | A * | 12/1982 | Bouchaudon et al. | 514/21.91 |
| 4,908,353 | A | 3/1990 | Yamamoto et al. | 514/19 |
| 5,624,894 | A | 4/1997 | Bodor | 514/2 |
| 5,629,288 | A * | 5/1997 | Lattrell et al. | 514/2.9 |
| 5,798,337 | A | 8/1998 | Somers et al. | 514/19 |
| 5,972,924 | A | 10/1999 | Keep et al. | 514/183 |
| 6,241,963 | B1 | 6/2001 | Kung et al. | 424/1.65 |
| 6,403,602 | B1 | 6/2002 | Crooks et al. | 514/282 |
| 6,548,484 | B1 | 4/2003 | Christian | 514/25 |
| 6,683,169 | B2 | 1/2004 | Knipp et al. | 536/23.5 |
| 6,703,381 | B1 * | 3/2004 | Ekwuribe et al. | 514/182 |
| 7,544,666 | B2 * | 6/2009 | Lee et al. | 514/1.1 |
| 2002/0013266 | A1 | 1/2002 | Bentley et al. | 514/2 |
| 2003/0130205 | A1 | 7/2003 | Christian | 514/23 |
| 2003/0144207 | A1 | 7/2003 | Bentley et al. | 514/12 |
| 2003/0216466 | A1 | 11/2003 | Scheuerman et al. | 514/513 |
| 2004/0033252 | A1 | 2/2004 | Yamamoto et al. | 424/8 |
| 2004/0092575 | A1 | 5/2004 | Peuvot et al. | 514/8 |
| 2004/0110735 | A1 | 6/2004 | Ekwuribe et al. | 514/8 |
| 2004/0142856 | A1 | 7/2004 | DeFrees et al. | 514/8 |
| 2004/0156859 | A1 | 8/2004 | Ezrin et al. | 424/185.1 |
| 2004/0185103 | A1 | 9/2004 | Lewis et al. | 424/486 |

FOREIGN PATENT DOCUMENTS

WO WO 2005113600 A2 * 12/2005

OTHER PUBLICATIONS

Solomons, Organic Chemistry, 6th Edition, Ch. 1, Carbon Compounds and Chemical Bonds, John Wiley and Sons, Inc. 1996.*

T. Bisogno, D. Melck, M. Bobrov, N. Gretskaya, V. Bezuglov, L. DePetrocellis, V. Di. Marzo; "N-acyl-dopamines: novel synthetic CB1 cannabinoid-receptor ligands and inhibitors of anandamide inactivation with cannabimimetic activity in vitro and in vivo," Biochem. J., vol. 351, 2000, pp. 817-824.

W. Pardridge; "Blood-Brain Barrier Drug Targeting: The Future of Brain Drug Development," Molecular Interventions, vol. 3, No. 2, Mar. 2003, pp. 90-105.

T. Sheskin, L. Hanus, J. Slager, Z. Vogel, R. Mechoulam; "Structural Requirements for Binding of Anandamide-Type Compounds to the Brain Cannabinoid Receptor," J. Med. Chem., vol. 40, 1997, pp. 659-667.

Y. Segall, G. Quistad, D. Nomura, J. Casida; "Arachidonylsulfonyl Derivatives as Cannabinoid CB1 Receptor and Fatty Acid Amide Hydrolase Inhibitors," Bioorg. Med. Chem. Lett. 13, 2003, pp. 3301-3303.

S. Lin, A. Khanolkar, P. Fan, A. Goutopoulos C. Qin, D. Papabadjis, A. Makriyannis; "Novel Analogues of Arachidonylethanolamide (Anandamide): Affinities for the CB1 and CB2 Cannabinoid Receptors and Metabolic Stability," J. Med. Chem., vol. 41, 1998, pp. 5353-5361.

S. Palmer, a. Khanolkar, A. Mikriyannis; "Natural and Synthetic Endocannabinoids and Their Structure-Activity Relationships," Current Pharmaceutical Design, vol. 6, 2000, pp. 1381-1397.

A. Howlett, F. Barth, T. Bonner, G. Cabral, P. Casellas, W. Devane, C. Felder, M. Herkenham, K. Mackie, B. Martin, R. Mechoulam, R. Pertwee; "International Union of Pharmacology. XXVIL Classification of Cannabinoid Receptors," Pharmacological Reviews, vol. 54, No. 2, 2002, pp. 161-202.

L. DePetrocellis, T. Bisogno, V. DiMarzo; "Endocannabinoids," Cannabinoids, 2004, pp. 98-130.

R. Razdan; "Chemistry and Structure ActivityRelationships for Tetrahydrocannabinols and Endocannabinoids," Cannabinoids, 2004, pp. 131-145.

(Continued)

*Primary Examiner* — Christina Bradley
*Assistant Examiner* — Jeanette Lieb
(74) *Attorney, Agent, or Firm* — Patent Procurement Services

(57) ABSTRACT

A compound provided by the present invention includes an endocannabinoid, endocannabinoid derivative, or endocannabinoid analog moiety covalently bonded to a biologically active peptide. One example of an inventive compound described is a conjugate of an endocannabinoid, endocannabinoid derivative, or endocannabinoid analog moiety covalently coupled to an opioid peptide, such as an endorphin, enkephalin, dynorphin or endomorphin. Also detailed are processes for making the described conjugates and pharmaceutical compositions including such compounds.

5 Claims, No Drawings

OTHER PUBLICATIONS

G. Friedrichsen, C. Nielsen, B. Staffansen, M. Begtrup; "Model prodrugs designed for the intestinal peptide transporter. A synthetic approach for coupling of hydroxy-containing compounds to dipeptides." European Journal of Pharmaceutical Sciences, vol. 14, 2001, pp. 13-19.
S. Huang, T. Bisogno, T. Petros, S. Chang, P. Zavitsanos, R. Zipkin, R. Sivakumar, A. Coop, D. Maeda, L. DePetrocellis, S. Burstein, V. DiMarzo, J. Walker; "Identification of a New Class of Molecules, the Arachidonyl Amino Acids, and Characterization of One Member that Inhibits Pain," Journal of Biological Chemistry, vol. 276, No. 46, Nov. 2001, pp. 42639-42644.
T. Fouad; "New research published this week in the Lancet Medical Journal suggests that ibuprofen may counteract the antiplatelet activities of aspirin." www.thedoctorslounge.net, Feb. 16, 2003.
S. Mojumdar, M. Melnik, E. Jona, D. Hudecova; "Preparation and Properties of Magnesium(II) Compounds with Some Bioactive Ligands," Chem. Papers 53(4), 1999, pp. 265-271.
M. Schmidt, A. Schier, H. Schmidbaur; "Magnesium Bis[D(−)-Mandelate] Dihydrate and Other Alkaline Earth, Alkali, and Zinc Salts of Mandelic Acid," Z. Naturforsch. 53 b, Jul. 1998.
R. Kassab, B. Fenet, H. Fessi, H. Parrot-Lopez; "Synthesis and characterisation of poly (L-lactic acid) galactosyl derivatives; access to functionalised microspheres," Tetrahedron Letters, 41(6), 2000, pp. 877-881.
N. Suvorov, et al.; "Bioorganicheskaya Khimiya," 2(6), 1976, pp. 729-736.
J. Aronson; "Potassium channels in nervous tissue," Biochem. Pharmacol. 43(1):11-4 (Jan. 9, 1992) (Abstract).
I. Grijalva et al.; "Efficacy and safety of r-aminopyridine in patients with long-term spinal cord injury; a randomized, double-blind, placebo-control trial," Pharmacotherapy 23(7):823-34 (Jul. 2003) (Abstract).
C. Bever, Jr.; "The current status of studies of aminopyridines in patients with multiple sclerosis," Ann. Neurol. 36 Suppl:S118-21 (1994) (Abstract).
W. Young; "Diaminopyride Treatment of Neurological Disorders," from http://carecure.rutgers.edu/spinewire/Articles/DAP/DAP.htm (Mar. 17, 2003).
"Release of Transmitters from Synaptic Vesicles," from http://www.ncbi.nlm.nih.gov/entrez . . . (2001).
W. Pan, A. Kastin; "Polypeptide delivery across the blood-brain barrier," Curr. Drug Targets CNS Nerol. Disord., Apr. 2004, (2):131-6, (Abstract).
L. Schechter; "The Potassium Channel Blockers 4-Aminopyridine and Tetraethylammonium Increase the Spontaneous Basal Release of [3H]5-Hydroxytryptamine in Rat Hippocampal Slices," J. Pharmacol. Exp. Ther. , vol. 282, No. 1, 1997, pp. 262-270.
J. Poduslo, G. Curran, C. Berg; "Macromolecular permeability across the blood-nerve and blood-brain barriers," Proc. Natl. Acad. Sci. USA, vol. 91, Jun. 1994, pp. 5705-5709.
G. Lee, S. Dallas, M. Hong, R. Bendayan; "Drug Transporters in the Central Nervous System: Brain Barriers and Brain Parenchyma Considerations," Pharmacological Reviews, vol. 53, No. 4, 2001, pp. 569-596.
W. Banks, M. Tschop, S. Robinson, M. Heiman; "Extent and Direction of Ghrelin Transport Across the Blood-Brain Barrier is Determined by its Unique Primary Structure," J. Pharmacol. Exp. Ther., vol. 302, No. 2, 2002, pp. 822-827.
W. Pardridge, "Blood-brain barrier carrier-mediated transport and brain metabolism of amino acids," Neurochem. Res. 23(5), May 1998, pp. 635-644 (Abstract).
M. Grimaldi, M. Atzori, P. Ray, D. Alkon; "Mobilization of Calcium from Intracellular Stores, Potentiation of Neurotransmitter-Induced Calcium Transients, and Capacitive Calcium Enry by 4-Aminopyridine," J. Neuroscience, May 2001, 21(9), pp. 3135-3143.
Q. Smith; "Transport of Glutamate and Other Amino Acids at the Blood-Brain Barrier," American Society for Nutritional Sciences, 130:1016S-22S, 2000.
J. Halter, A. Blight, W. Donovan, O. Calvillo; "Intrathecal administration of 4-aminopyridine in chronic spinal injured patients," Spinal Cord, 38(12), Dec. 2000, pp. 728-732 (Abstract).
K. Hayes, P. Potter, R. Hansebout, J. Bugaresti, J. Hsieh, S. Nicosia, M. Katz, A. Blight, R. Cohen; "Pharmacokinetic studies of multiple oral doses of fampridine-SR in patients with chronic spinal cord injury," Clin. Neuropharmacol., Jul.-Aug. 2003, 26(4), pp. 185-192 (Abstract).
J. Segal, K. Hayes, S. Brunnemann, J. Hsieh, P. Potter, M. Pathak, D. Tierney, D. Mason; "Absorption characteristics of sustained-release 4-aminopyridine (fampridine SR) in patients with chronic spinal cord injury," J. Clin. Pharmacol., 40, 2000, pp. 402-409.
Q. Lin, D. Jo, K. Gebre-Amlak, H. Ruley; "Enhanced cell-permant Cre protein for site-specific recombination in cultured cells," BioMed Central Biotechnology, 4:25, pp. 1-13.

* cited by examiner

ENDOCANNABINOID CONJUGATE AND A PHARMACEUTICAL COMPOSITION FOR TREATMENT OF NEURONAL DISORDERS

REFERENCE TO RELATED APPLICATIONS

This application is a continuation-in-part of U.S. patent application Ser. No. 11/023,196, filed Dec. 27, 2004, which claims priority from U.S. Provisional Patent Application Ser. No. 60/609,659, filed Sep. 14, 2004. This application is also a continuation-in-part of U.S. patent application Ser. No. 11/023,241, filed Dec. 27, 2004; Ser. No. 11/023,240, filed Dec. 27, 2004; and Ser. No. 11/023,309, filed Dec. 27, 2004. The entire content of each application is incorporated herein by reference.

FIELD OF THE INVENTION

The invention relates to endocannabinoid conjugate compositions and processes for preparation thereof. In particular, the invention relates to endocannabinoid-peptide conjugates and processes for preparation of said conjugates.

BACKGROUND OF THE INVENTION

A well-known problem in treatment of neurological disorders is ineffective delivery of therapeutic agents to neurons and associated cells due to the blood-brain and blood-nerve barriers. Considerable development has gone into the development of drugs and delivery systems for the transport of pharmacologically active species to overcome this limitation. To date, while several approaches have shown promise, surprisingly little therapeutic progress has been made with respect to delivery of a therapeutic agent to treat neurological conditions or diseases where transport to a target cell is inhibited by the blood-brain and blood-nerve barriers.

In particular, there are inherent difficulties in the effective administration of peptide therapeutic agents and/or their derivative, or analogs. Peptides often do not easily cross the blood brain barrier and, accordingly, their activity in the central nervous system after oral or parenteral administration is generally inhibited. In addition, many peptide agents have activity at sites external to the central nervous system which may contribute to clinical side effects. Since higher doses are required to create a therapeutic effect because of poor penetration of the blood brain barrier, a frequent consequence is that the higher doses may increase systemic toxicity and/or undesired side effects.

Extra-CNS side effects noted with the systemic administration of peptide agents can be largely averted by utilizing intrathecal drug delivery since intrathecal delivery to the lumbar or mid-thoracic spinal intrathecal space concentrates the medication in the lower area of the spinal cord cerebrospinal fluid at much higher levels than those attainable via the oral route of administration (Meythaler, McCary, Hadley, J. Neurosurg. 1997; 87(3):415-9). Typically, the type of delivery system for intrathecal therapy consists of a subcutaneously placed pump having a reservoir which is attached to an intraspinal catheter. This drug delivery methodology concentrates the medication within the spinal subarachnoid space and the thoracolumbar and sacral spinal regions at a much higher level than that attainable via the oral route of administration. Meythaler et al., J. NeuroSurgery 1997; 87:415-9. From the subarachnoid space, the cerebrospinal fluid then flows to the arachnoid villi for reabsorption thereby avoiding a significant part of the cerebral hemispheres. Meythaler et al., Arch. Phys. Med. Rehabil. 1996; 77:461-466. Only low levels of the medication have the potential to reach the brainstem or cerebrum as studies have demonstrated the lumbar-to-cisternal drug cerebrospinal fluid (CSF) drug concentration gradient is 4.1:1. Kroin et al., Parenteral Drug Therapy in Spasticity and Parkinson's Disease 1991, pp. 73-83. By utilizing intrathecal drug delivery, the cognitive side effects of oral drug delivery, such as drowsiness and lethargy, can be avoided. Coffey et al., J. Neurosurg. 1993; 78:226-232; Penn et al., N. Engl. J. Med. 1989; 320:1517-1522; Knuttson et al., J. Neurol. Sci. 1974; 23:473-484. Furthermore, intraventricular delivery does the same for the periventricular area or region of the brain.

Despite certain advantages of the intrathecally delivered peptide agents, patients often prefer an oral or systemically administered therapeutic agent as less invasive, particularly where the condition is chronic. Further, many peptides have beneficial and desirable effects on cells external to the CNS, such that simultaneous treatment of disorders in both the CNS and external to the CNS is desirable and may be addressed by systemic administration of a composition.

Thus, there exists a need for improved compositions for systemic, intrathecal and/or intraventricular delivery of a peptide therapeutic agent.

SUMMARY OF THE INVENTION

A compound is provided by the present invention which includes an endocannabinoid moiety covalently bonded to a biologically active peptide. An endocannabinoid moiety included has the formula $R_1$ - $R_2$ where $R_1$ is a $C_{14}$-$C_{28}$ optionally substituted alkenyl moiety having at least two double bonds, and $R_2$ is a moiety selected from C(═O)NH$R_3$; C(═O)O$R_3$; $CH_2OR_3$ and NHC(═O)$R_3$, where $R_3$ is straight chain or branched, substituted or unsubstituted $C_1$-$C_5$ alkyl; $C_1$-$C_5$ alkenyl; $C_1$-$C_5$ alkynyl or $C_6$-$C_{13}$ alkylaryl, alkenylaryl or alkynlaryl.

In a particular example of an inventive compound, the $R_1$ moiety of the endocannabinoid has the formula $R_4(CR_5R_6)_x$ $(CH{=}CHCH_2)_y(CH_2)_v(CH{=}CHCH_2)_w(CH_2)_z$— where x is an integer in the range of 1-8, inclusive, y is an integer in the range from 1-6, inclusive, z is an integer in the range from 1-6, inclusive, v is an integer in the range from 0-1, w is an integer in the range from 0-1, $R_4$ is $CH_3$ or CN, and where $R_5$ and $R_6$ are each independently H or $CH_3$.

In a further example, the $R_2$ moiety of the endocannabinoid is selected from C(═O)NH$R_3$; C(═O)O$R_3$; $CH_2OR_3$ and NHC(═O)$R_3$, where $R_3$ is straight chain or branched, substituted or unsubstituted: $C_1$-$C_5$ alkyl, alkenyl or alkynyl; $C_1$-$C_5$ hydroxyalkyl, hydroxyalkenyl or hydroxyalkynyl; $C_1$-$C_5$ alkoxyalkyl, alkoxyalkenyl or alkoxyalkynyl; $C_1$-$C_5$ aminoalkyl, aminoalkenyl or aminoalkynyl; $C_6$—$Cl_3$ alkylaryl, alkenylaryl or alkynlaryl; $C_6$-$C_{13}$ alkylhydroxyaryl, alkenylhydroxyaryl or alkynylhydroxyaryl; $C_6$-$C_{13}$ alkylaminoaryl, alkenylaminoaryl or alkynylaminoaryl.

Specific illustrations of the $R_2$ moiety include the following: C(═O)NH$CH_2CH_2OH$; C(═O)NHCH$(CH_2OH)_2$; $CH_2OCH(CH_2OH)_2$; C(═O)O$CH_2CH_2NH_2$; C(═O)OCH $(CH_2OH)_2$; C(═O)NHCH$(CH_3)CH_2OH$; C(═O) NH$CH_2CH_2$L, where L is a halogen atom; C(═O)$CL_3$, where L is a halogen atom; C(═O)NH$CH_2CHCH_2$ and C(═O)NH$CH_2CH_2$(3,4$(OH)_2C_6H_3$.

As noted above, a provided inventive compound is a conjugate of an endocannabinoid and a biologically active peptide. Such a biologically active peptide is optionally a hormone, a neurotrophic factor, a neuroactive peptide or an opioid peptide. Particularly preferred are peptides having an analgesic activity. In one embodiment, an opioid peptide is selected from the group consisting of: an enkephalin, an endorphin, an endomorphin and a dynorphin. Specific examples of opioid peptides include dermorphin, dermenkephalin, deltorphin I, deltorphin II, Leu enkephalin, Met enkephalin, dynorphin A, dynorphin B, alpha-neoendorphin, beta.-neoendorphin, metorphamide, beta-endorphin, DAMGO, DPDPE, DSLET , DADL, CTOP, FK-33824, morphiceptin, DALCE, endomorphin-1, endomorphin-2, beta.-casomorphin, DALDA, PL017, DAGO, hemorphin-4, CTP, CTAP, TAPS, MIF-1, Tyr-MIF-1, Tyr-W-MIF-1, Tyr-Pro-Trp and Tyr-Pro-Trp-Gly (SEQ ID NO: 33).

Additionally provided are conjugates of an endocannabinoid and a peptide such as bradykinin, bombesin, calcitonin, cholecystokinin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide, calcitonin gene-related peptide, corticotropin, corticotropin-releasing hormone, delta sleep-inducing peptide, galanin-like peptide, gastric inhibitory polypeptide, gastrin-releasing peptide, gastrins, gonadorelin, melanocyte stimulating hormone (MSH), MSH release-inhibiting hormone, MSH-releasing hormone, pancreatic polypeptide, peptide PHI, pituitary hormone release inhibiting hormones, pituitary hormone-releasing hormones, prolactin release-inhibiting hormone, prolactin-releasing hormone, protirelin, somatomedins, somatotropin-releasing hormone, a tachykinin, nerve growth factor (NGF), brain-derived neurotophic factor (BDNF), ciliary neurotrophic factor (CNTF), epidermal growth factor, ghrelin, granulocyte macrophage-colony stimulating factor (GM-CSF), fibroblast growth factors (FGF), platelet-derived growth factors (PDGF), glia-derived neurotrophic factor (GDNF), insulin-like growth factors such as IGF-1, interleukins such as IL-1a, IL-1b, leptin, luteinizing hormone releasing hormone (LHRH), leukemia inhibitory factor (LIF), neurotrophin 3 (NT3) neurotrophin 4/5 (NT4/5), and pituitary adenylate cyclase-activating polypeptide (PACAP).

A compound is provided in which an endocannabinoid and a biologically active peptide are covalently coupled. In one option, the endocannabinoid and peptide are coupled by a peptide bond. In a further option, the endocannabinoid and peptide are coupled through an ester linkage. In yet another option, the endocannabinoid and peptide are coupled through a linker having a covalent bond to the biologically active peptide and a covalent bond to the endocannabinoid. The linker may further include a pendent substituent, the pendent substituent having at least one detectable marker moiety such as a radioactive atom, a spectroscopically active marker, and an organic dye.

Further described is an inventive pharmaceutical composition including a compound in which an endocannabinoid and a biologically active peptide are covalently coupled, along with a pharmaceutically acceptable carrier.

Processes for forming an endocannabinoid-biologically active peptide conjugate are described. In one embodiment, an inventive process includes reacting an endocannabinoid and a biologically active peptide to covalently couple the endocannabinoid and the biologically active peptide. Optionally. a coupling agent, such as a carbodiimide is included in a reaction to couple an endocannabinoid and a peptide.

In a further option, a coupling agent in the form of a linker is used to couple an endocannabinoid and a peptide indirectly.

DETAILED DESCRIPTION OF THE INVENTION

The present invention provides methods and compositions for treating conditions or disorders having a neurological component such as neuronal disease, cancer, digestive disorders, immune disease and symptoms or sequelae thereof. In particular, methods and compositions are provided for treating brain trauma, cerebrovascular accident, demyelinating disease, epilepsy, glaucoma, glutamate-mediated excitotoxicity, hypoxia, multiple sclerosis, spinal cord disorders, neurodegenerative diseases, pain, oncologic and AIDS-related sequelae such as nausea, vomiting and anorexia; and gastrointestinal diseases, including Crohn's disease, gastric ulcers, gastroesophageal reflux disease, irritable bowel syndrome, paralytic ileus, and secretory diarrhea. Symptoms such as inflammation, immunosuppression, convulsion, high intraocular pressure, nausea, vomiting, depression, pain, dystonia/spasticity, spastic disorders, convulsive disorders, tardive dyskinesia, and insomnia are treated by administration of a therapeutically effective amount of an inventive compound to a patient or subject having a neurological disease, cancer, digestive disorder, immune disease or symptoms or sequelae thereof such as listed above.

The terms "patient" and "subject" are synonymous and include any of a variety of organisms, mammals being particularly preferred. Suitable mammals include, but are not limited to, rodents, such as rats, mice, hamsters, and guinea pigs; primates; farm animals, such as sheep, goats, pigs, cows, and horses; common domestic animals such as dogs and cats; and in a particularly preferred embodiment, humans.

A therapeutically effective amount is defined as an amount of an inventive conjugate compound conjugate that when administered to a patient or subject, ameliorates a condition or symptom described herein.

The terms "biologically active peptide" and "peptide therapeutic agent" are synonymous as used herein and are intended to mean a natural or synthetic compound containing two or more amino acids. Amino acids present in a biologically active peptide include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, allo-hydroxylysine, allo-isoleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyclobutyl alanine, cyclohexylalanine, cyclohexylglycine, N5-aminocarbonylornithine, cyclopentyl alanine, cyclopropyl alanine, 3-sulfoalanine, 2,4-diaminobutanoic acid, diaminopropionic acid, 2,4-diaminobutyric acid, diphenyl alanine, N,N-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohistidine, 2-hydroxyisovaleric acid, homophenylalanine, homoleucine, homoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mercaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3-(4-sulfophenyl)propionic acid, 1-amino-1-carboxycyclopentane, 3-thienylalanine, epsilon-N-trimethyllysine, 3-thiazolylalanine, thiazolidine 4-carboxylic acid, alpha-amino-2,4-dioxopyrimidinepropanoic acid, and 2-naphthylalanine. Accordingly, the term "biologically active peptide" as used herein includes peptides having between 2 and about 100 amino acids and having a molecular weight in the range of about 150-10,000 daltons.

A biologically active peptide is obtained by any of various methods known in the art illustratively including isolation from a cell or organism, chemical synthesis, expression of a nucleic acid and partial hydrolysis of proteins. Chemical methods of peptide synthesis are known in the art and include solid phase peptide synthesis and solution phase peptide synthesis for instance. A biologically active peptide included in an inventive composition may be a naturally occurring or non-naturally occurring peptide. The term "naturally occurring" refers to a peptide endogenous to a cell, tissue or organism and includes allelic variations. A non-naturally occurring peptide is synthetic or modified and is not found in an unmodified cell, tissue or organism.

The term "biological activity" as used herein is intended to mean an activity usually associated with a peptide. Biological activity includes activity described at a molecular level such as receptor binding/blocking, receptor activation/inhibition, ion channel modulation and second messenger modulation. Biological activity further includes activity described at a cellular or subcellular level such as stimulation/inhibition of synaptic release. In addition, biological activity further includes activity described at an organismal level such as behavioral changes, changes in perception of pain, and decreased nausea and/or vomiting. Biological activity of a peptide is measurable and may be assessed by techniques known in the art. In the context of an inventive conjugate, a peptide having biological activity is described as a biologically active peptide.

The term "covalently coupled" as used herein is intended to mean that the coupled moieties are directly bonded to each other, or indirectly bonded to each other, such as by a linker.

The term "linkage" as used herein is intended to mean a bond or group formed by chemical reaction between two moieties such that the moieties are covalently coupled.

Compounds

An inventive conjugate is provided in which an endocannabinoid (EC) is covalently coupled to a biologically active peptide (P). The term "endocannabinoid" as used herein is intended to refer to endocannabinoids as well as endocannabinoid derivative, or analogs thereof as described herein.

Endocannabinoids are compounds found in vivo and include anandamide, virodhamine, docosatetraenoyl-ethanolamide, di-homo-□-linolenoyl-ethanolamide, 2arachidonoyl-glycerol, and nolodin ether. A derivative or analog of an endocannabinoid is a molecule having a structure as defined herein and having biological activity at a cannabinoid receptor. A derivative, or analog of an endocannabinoid is determined to have biological activity at a cannabinoid receptor by any of various methods of biological activity assays known in the art. For instance, biological activity may be measured as the ability of a compound to specifically bind to a cannabinoid receptor. Receptor binding may be measured as the extent of displacement of an endocannabinoid or exogenous cannabinoid at a receptor. An example of such a binding assay is described in Sheskin, T. et al., (1997), J. Med. Chem. 40:659-667. Endocannabinoids and synthetic derivatives, or analogs thereof are described in references such as Palmer, S. L. et al., Current Pharmaceutical Design, 6:1381-1397, 2000; Howlett, A. C. et al., Pharmacological Reviews, 54(2):161-202, 2002; Di Marzo, V. (Ed.), Cannabinoids, Kluwer Academic/Plenum Publishers, NY, N.Y., 2004, particularly the chapter by Di Petrocellis, L. et al. entitled Endocannabinoids; Bisogno, T. et al., Biochem. J., 351:817-824, 2000; Sheskin, T. et al., (1997), J. Med. Chem. 40:659-667; Lin, S. et al., (1998), J. Med. Chem. 41:5353-5361; and U.S. Pat. Nos. 5,618,955; 5,688,825; 6,284,788; 6,348,498 and 6,531,636. Endocannabinoids may be isolated from tissues or cells, or synthesized. Synthesis of endocannabinoids and derivatives, or analogs thereof is described in references such as Sheskin, T. et al., (1997), J. Med. Chem. 40:659-667; and Lin, S. et al., (1998), J. Med. Chem. 41:5353-5361.

In one embodiment, the endocannabinoid or derivative, or analog, or analog thereof, EC, has the formula $R_1$—$R_2$ where $R_1$ is a $C_{14}$-$C_{28}$ optionally substituted alkenyl moiety having at least two double bonds, and $R_2$ is a moiety selected from $C(=O)NHR_3$; $C(=O)OR_3$; $CH_2OR_3$ and $NHC(=O)R_3$, where $R_3$ is straight chain or branched, substituted or unsubstituted $C_1$-$C_5$ alkyl; $C_1$-$C_5$ alkenyl; $C_1$-$C_5$ alkynl or $C_6$-$C_{13}$ alkylaryl, alkenylaryl or alkynlaryl. In a preferred embodiment, the double bonds present in the moiety $R_1$ are in the cis configuration.

In a particular example, the EC moiety $R_1$ has the formula $R_4(CR_5R_6)_x(CH{=}CHCH_2)_y(CH_2)_v(CH{=}CHCH_2)_w(CH_2)_z$ — where x is an integer in the range of 1-8, inclusive, y is an integer in the range from 1-6, inclusive, z is an integer in the range from 1-6, inclusive, v is an integer in the range from 0-1, w is an integer in the range from 0-1, $R_4$ is $CH_3$ or CN, and where $R_5$ and $R_6$ are each independently H or $CH_3$.

In a particular example, the EC moiety $R_2$ is a moiety selected from $C(=O)NHR_3$; $C(=O)OR_3$; $CH_2OR_3$ and $NHC(=O)R_3$, where $R_3$ is straight chain or branched, substituted or unsubstituted: $C_1$-$C_5$ alkyl, alkenyl or alkynyl; $C_1$-$C_5$ hydroxyalkyl, hydroxyalkenyl or hydroxyalkynyl; $C_1$-$C_5$ alkoxyalkyl, alkoxyalkenyl or alkoxyalkynl; $C_1$-$C_5$ aminoalkyl, aminoalkenyl or aminoalkynl; $C_6$-$C_{13}$ alkylaryl, alkenylaryl or alkynlaryl; $C_6$-$C_{13}$ alkylhydroxyaryl, alkenylhydroxyaryl or alkynylhydroxyaryl; $C_6$-$C_{13}$ alkylaminoaryl, alkenylaminoaryl or alkynylaminoaryl. Specific illustrative examples of the EC moiety $R_2$ include: $C(=O)NHCH_2CH_2OH$; $C(=O)NHCH(CH_2OH)_2$; $CH_2OCH(CH_2OH)_2$; $C(=O)OCH_2CH_2NH_2$; $C(=O)OCH(CH_2OH)_2$; $C(=O)NHCH(CH_3)CH_2OH$; $C(=O)NHCH_2CH_2L$, where L is a halogen atom; $C(=O)CL_3$, where L is a halogen atom; $C(=O)NHCH_2CHCH_2$ and $C(=O)NHCH_2CH_2(3,4(OH)_2C_6H_3$.

Exemplary endocannabinoids and synthetic derivative, or analogs include compounds having the following chemical structures:

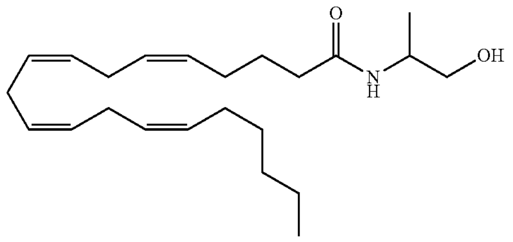

-continued
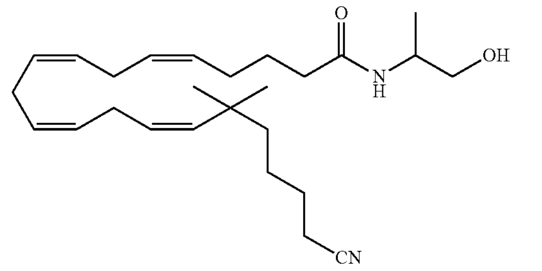
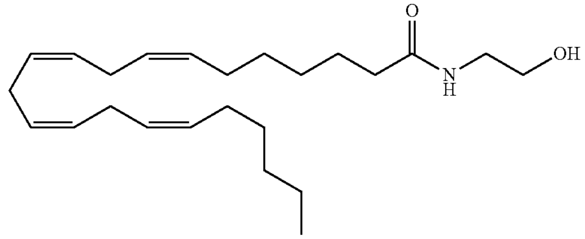
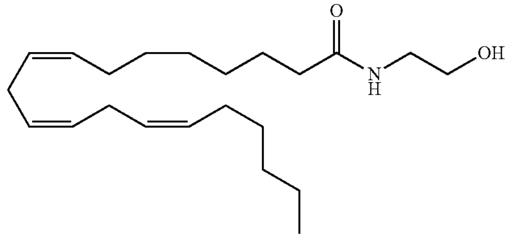
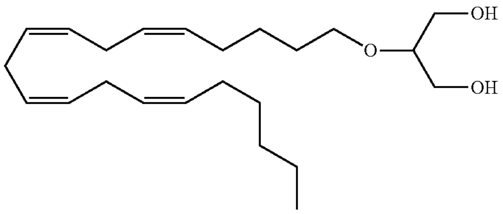
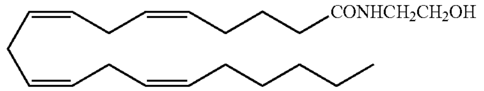
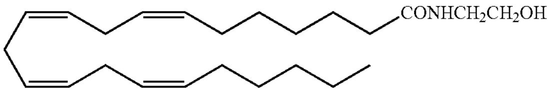
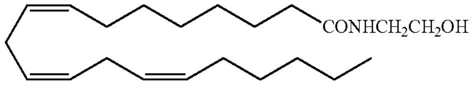
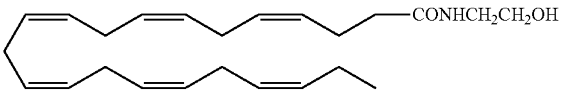
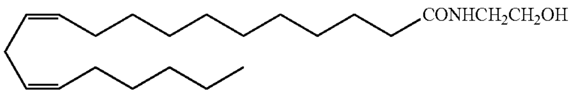
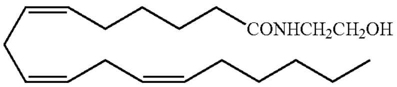
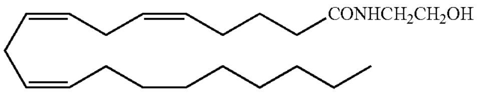
-continued
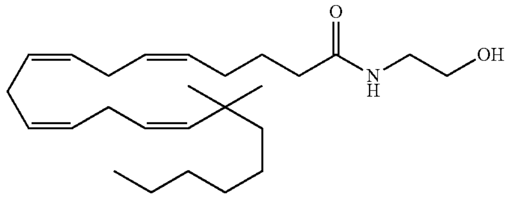
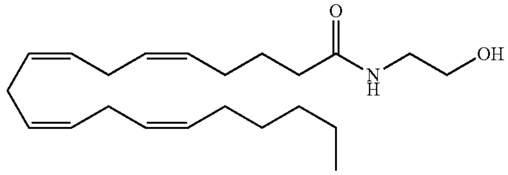
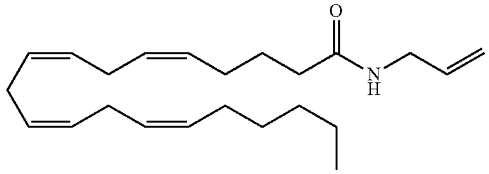
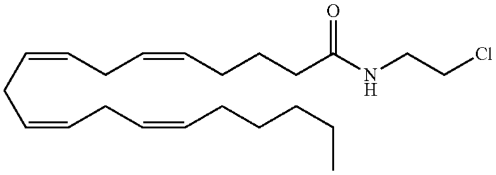
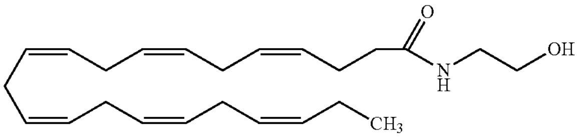
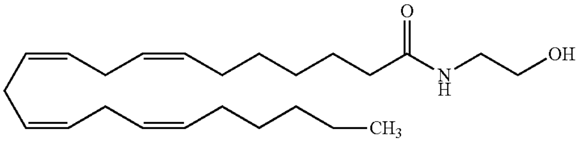
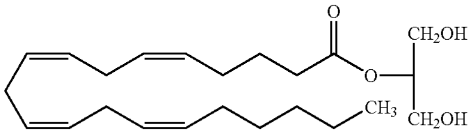
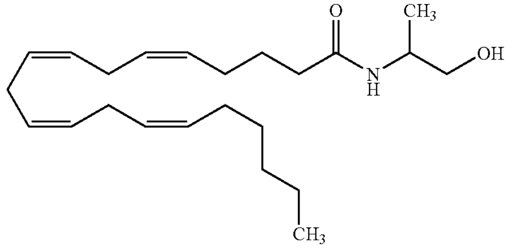
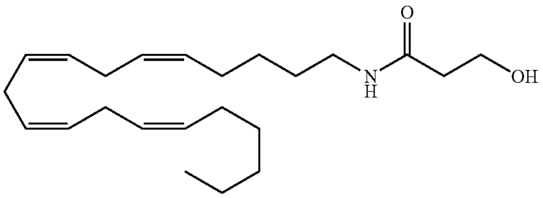
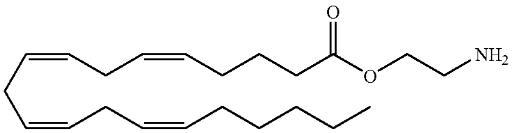

-continued

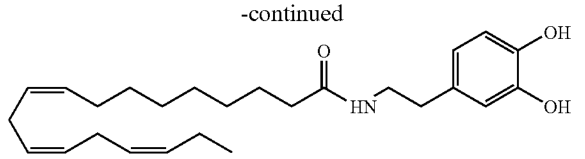

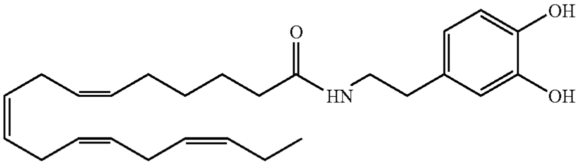

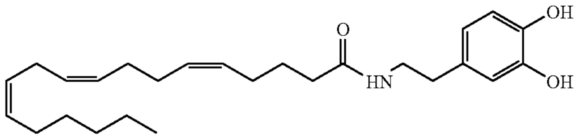

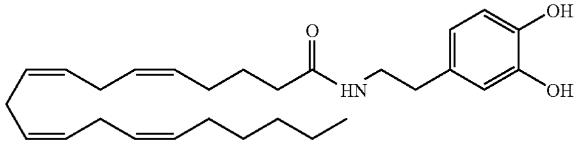

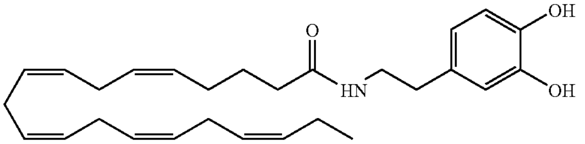

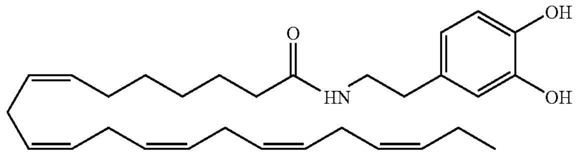

As noted above, an inventive compound is a conjugate of a moiety EC and a biologically active peptide, P. A particularly preferred peptide is a peptide having in vivo activity associated with alleviation or amelioration of a symptom of a condition or disease as noted above.

In a particular embodiment, the peptide, P, is a peptide having in vivo activity associated with alleviation or amelioration of pain. Optionally, the peptide is an opioid peptide. As used herein the term "opioid peptide" is intended to mean a peptide which is an opiate receptor ligand having agonist or antagonist activity. Opiate receptors include mu (μ), kappa(κ) and delta (Δ) opiate receptors and their various subtypes, as well as the "orphan receptor" ORL. A preferred opioid peptide is an agonist of an opiate receptor. Details of opiate receptors and ligands thereof is found in standard reference texts such as Goodman and Gilman's The Pharmacological Basis of Therapeutics 10th ed., J. G. Harman et al., Eds., McGraw-Hill, New York, 2001.

Exemplary opioid peptides include an enkephalin, an endorphin, an endomorphin or a dynorphin. Illustrative examples of opioid peptides include dermorphin, dermenkephalin, deltorphin I, deltorphin II, Leu enkephalin, Met enkephalin, dynorphin A, dynorphin B, alpha-neoendorphin, beta.-neoendorphin, metorphamide, beta-endorphin, DAMGO, DPDPE, DSLET , DADL, CTOP, FK-33824, morphiceptin, DALCE, endomorphin-1, endomorphin-2, beta.-casomorphin, DALDA, PL017, DAGO, hemorphin-4 , CTP, CTAP, TAPS, MIF-1, Tyr-MIF-1, Tyr-W-MIF-1, and fragments of Tyr-W-MIF-1 such as Tyr-Pro-Trp and Tyr-Pro-Trp-Gly (SEQ ID NO: 33).

Examples of specific amino acid sequences of opioid peptides include dermorphin: (Tyr-D -Ala-Phe-Gly-Tyr-Pro-Ser-$NH_2$) (SEQ ID NO: 1), dermenkephalin; (Tyr-D-Met-Phe-His-Leu- Met-Asp-$NH_2$) (SEQ ID NO: 2), deltorphin I (Tyr-D-Ala-Phe-Asp-Val-Val-Gly-$NH_2$) (SEQ ID NO: 3), deltorphin II (Tyr-D-Ala-Phe-Glu-Val-Val-Gly-$NH_2$) (SEQ ID NO: 4), Leu enkephalin (Tyr-Gly-Gly-Phe-Leu) (SEQ ID NO: 5), Met enkephalin (Tyr-Gly-Gly-Phe-Met) (SEQ ID NO: 6_1, dynorphin A (Tyr-Gly-Gly-Phe-Leu-Arg-Arg-Ile-Arg-Pro-Lys-Leu-Lys-Trp-Asp-Asn-G1n) (SEQ ID NO: 7), dynorphin B (Tyr-Gly-Gly-Phe-Leu-Arg-Arg-Gln-Phe-Lys-Val-Val-Thr) (SEQ ID NO: 8), alpha-neoendorphin (Tyr-Gly-Gly-Phe-Leu-Arg-Lys-Tyr-Pro-Lys) (SEQ ID NO: 9), beta.-neoendorphin (Tyr-Gly-Gly-Phe-Leu-Arg-Lys-Tyr-Pro) (SEQ ID NO: 10), metorphamide (Tyr-Gly-Gly-Phe-Met-Arg-Arg-Val-$NH_2$) (SEQ ID NO: 11), beta-endorphin (Tyr-Gly-Gly-Phe-Met-Thr-Ser-Glu-Lys-Ser-Gln-Thr-Pro-Leu-Val-Thr-Leu-Phe-Lys-Asn-Ala-Ile-Ile-Lys-Asn-Ala-Tyr-Lys-Lys-Gly-Glu) (SEQ ID NO: 12), DAMGO (D-Ala2, MePhe4Gly(o1)5)enkephalin (SEQ ID NO: 13), DPDPE (D-$Pen^2$,D-$Pen^5$)enkephalin (SEQ ID NO: 14), DSLET (D-$Ser^2$,$Leu^5$)enkephalin-$Thr^6$ (SEQ ID NO: 15), DADL (D-$Ala^2$,D-$Leu^5$)enkephalin (SEQ ID NO:

CTOP (D-Phe-Cys-Tyr-D-Trp-Orn-Thr-Pen-Thr-$NH_2$) (SEQ ID NO: 17), FK-33824 (Tyr-Ala-Gly-MePhe-Met-OH)-enkephalin (SEQ ID NO: 18), morphiceptin (Tyr-Pro-Phe-Pro-$NH_2$) (SEQ ID NO: 19), DALCE [D-$Ala^2$,$Leu^5$, $Cys^6$Jenkephalin (SEQ ID NO: 20), endomorphin-1 (Tyr-Pro-Trp-Phe-$NH_2$) (SEQ ID NO: 21), endomorphin-2 (Tyr-Pro-Phe-Phe-$NH_2$) (SEQ ID NO: 22), beta.-casomorphin (Tyr-Pro-Phe-Val-Glu-Pro-Ile) (SEQ ID NO: 23), DALDA (Tyr-(D)Arg-Phe-Lys-$NH_2$) (SEQ ID NO: 24), PL017 (Tyr-Pro-(N-Me)Phe-(D)Pro-$NH_2$) (SEQ ID NO: 25), DAGO (T-Y-R (Tyr-D-Ala-Gly-N(Me)Phe-Gly-ol) (SEQ ID NO: 26), DSLET (Tyr-D-Ser-Gly-Phe-Leu-Thr) (SEQ ID NO: 27), hemorphin-4 (Tyr-Pro-Trp-Thr) (SEQ ID NO: 28), CTP (D-Phe-Cys-Tyr-D-Trp-Lys-Thr-Pen-Thr-$NH_2$) (SEQ ID NO: 29), CTAP (D-Phe-Cys-Tyr-D-Trp-Arg-Thr-Pen-Thr-$NH_2$) (SEQ ID NO: 30), TAPS (Tyr-D-Arg-Phe-Sar) (SEQ ID NO: 31), MIF-1 (Pro-Leu-Gly-$NH_2$), Tyr-MIF-1 (Tyr-Pro-Leu-Gly-$NH_2$) (SEQ ID NO: 32), Tyr-W-MIF-1 (Tyr-Pro-Trp-Gly-$NH_2$) (SEQ ID NO: 33), and fragments of Tyr-W-MIF-1 such as Tyr-Pro- Trp and Tyr-Pro-Trp-Gly (SEQ ID NO: 33). In the amino acid sequences herein, the amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine are indicated by the standard three letter abbreviations and where "Sar" indicates sarcosine (N-methylglycine), "Orn" indicates ornithine, and "Pen" indicates penicillamine (3-mercaptovaline). Generally, the above exemplary opioid peptide sequences are human peptides but exclusion of opioid peptides from other species is not intended by the inclusion of these examples.

In a further embodiment the biologically active peptide, P, is a neurotrophic factor or a hormone. Further specific examples of biologically active peptides include bradykinin, bombesin, calcitonin, cholecystokinin, insulin, gastrin, substance P, neurotensin, glucagon, secretin, somatostatin, motilin, vasopressin, oxytocin, prolactin, thyrotropin, an angiotensin, galanin, neuropeptide Y, thyrotropin-releasing hormone, gonadotropnin-releasing hormone, growth hormone-releasing hormone, luteinizing hormone, vasoactive intestinal peptide, calcitonin gene-related peptide, corticotropin, corticotropin-releasing hormone, delta sleep-inducing peptide, galanin-like peptide, gastric inhibitory polypeptide, gastrin-releasing peptide, gastrins, gonadorelin, melanocyte stimulating hormone (MSH), MSH release-inhibiting hormone, MSH-releasing hormone, pancreatic polypeptide, peptide PHI, pituitary hormone release inhibiting hormones, pituitary hormone-releasing hormones, prolactin release-inhibiting hormone, prolactin-releasing hormone, protirelin, somatomedins, somatotropin-releasing hormone, a tachykinin, nerve growth factor (NGF), brain-derived neurotophic factor (BDNF), ciliary neurotrophic factor (CNTF), epidermal growth factor, ghrelin, granulocyte macrophage-colony stimulating factor (GM-CSF), fibroblast growth factors (FGF), platelet-derived growth factors (PDGF), glia-derived neurotrophic factor (GDNF), insulin-like growth factors such as IGF-1, interleukins such as IL-1a, IL-1b, leptin, luteinizing hormone releasing hormone (LHRH), leukemia inhibitory factor (LIF), neurotrophin 3 (NT3) neurotrophin 4/5 (NT4/5), and pituitary adenylate cyclase-activating polypeptide (PACAP).

As noted above, an inventive conjugate is provided in which an endocannabinoid or derivative, or analog thereof (EC) having biological activity at a cannabinoid receptor is covalently coupled to a biologically active peptide (P). Where EC is represented by the formula $R_1$-$R_2$, a peptide P, is preferably conjugated to the $R_2$ moiety of EC by a covalent bond. For example, in one embodiment, a peptide linkage is created between EC and P by reacting an amine moiety of $R_2$ with a C-terminal carboxyl moiety of the peptide. In another embodiment, a covalent bond between the peptide and EC creates an ester moiety. For instance, an ester moiety is created between EC and P by reacting a hydroxyl moiety of $R_2$ with a C-terminal carboxyl moiety of P.

In another embodiment, an inventive compound includes a linker, L which links EC and P indirectly by a covalent bond between L and P, and a covalent bond between L and EC such that the compound has the formula EC-L-P. In one embodiment, a linker has an alkyl backbone of less than eight carbon atoms.

Optionally, an included linker has a pendent substituent, the pendent substituent having a marker moiety such as a radioactive atom, a spectroscopically active marker, or an organic dye.

Process for Forming an Inventive Compound

A process is provided for forming a conjugate between an endocannabinoid, derivative, or analog thereof, EC, and a biologically active peptide, P. A process for forming an inventive conjugate includes the step of reacting EC and a biologically active peptide, P, to form a conjugate.

Optionally, a step of reacting EC and P includes adding a coupling agent. In particular, where the EC moiety $R_2$ is $C_1$-$C_5$ aminoalkyl, aminoalkenyl, aminoalkynl, or $C_6$-$C_{13}$ aminoalkylaryl, aminoalkenylaryl, aminoalkynlaryl, a peptide bond is formed by reaction of the $R_2$ moiety $NH_2$ group and the C-terminal carboxyl group of the peptide in the presence of a coupling agent such as a carbodiimide. For example, where the EC is virodhamine which includes the EC $R_2$ moiety $COOCH_2CH_2NH_2$, a carbodiimide coupling agent may be used in a reaction to covalently couple virodhamine to a biologically active peptide. Carbodiimides are zero length cross-linkers that mediate the formation of an amide or phosphoramidate linkage between a carboxylate and an amine, or a phosphate and an amine, respectively. Chu, B., Kramer, F. & Orgel, L. "Synthesis of an amplifiable reporter RNA for bioassays," *Nucleic Acids Research* 1986; 14, 5591-5603. Hoare, D. & Koshland, D. E., *J. Am. Chem. Soc.* 1966; 88, 2057. Carbodiimides react with carboxylic acids to form highly reactive O-acylisourea compounds that are very short lived but react with nucleophiles to form an amide bond. Dicyclohexylcarbodiimide (DCCD) is representative of a reactive carbodiimide. This reaction works effectively between pH 4.5 and 7.5. Molecules with a phosphate group such as the 5' phosphate on oligonucleotides can also react with amine-containing groups by using the carbodiimide reaction.

In a further example, an inventive conjugate is formed by creating an amide linkage between a peptide in an acid chloride form and an $R_2$ amine group on the EC moiety $R_2$, for instance, where $R_2$ is $COOCH_2CH_2NH_2$. An acid chloride derivative, or analog of a biologically active peptide is produced, for instance, by reaction of a peptide with a chloride compound such as thionyl chloride, phosphorus trichloride or phosphorus pentachloride. Reaction of the acid chloride form of the peptide with an amine moiety present on EC may be performed in the presence of a tertiary amine chloride scavenger in order to form an EC-biologically active peptide conjugate. Tertiary amine chloride scavengers operative herein illustratively include pyridine, and trialkyl amines.

In addition, other reagents useful in forming an amide bond between two reactants are well known to the art. Methods for the preparation of an amide bond are described in Houben-Weyl, *Methoden der organischen Chemie* (*Methods of Organic Chemistry*), Volume 15/2; Bodanszky et al., in "Peptide Synthesis", E. Gross & J. Meienhofer (Eds), Academic Press, Y. Wiley, New York, 1976. Further reactions are detailed in R. C. Larock, Comprehensive Organic Transformations: A Guide to Functional Group Preparations, Wiley-VCH, 2nd ed., 1999.

It is appreciated that a protective group may be added to a reactant in a process to form a conjugate compound. For example, amine protective groups and the chemistry for the addition thereof are provided in *Protective Groups in Organic Synthesis* by T. W. Greene and P. G. M. Wuts, John Wiley & Sons, 1999 and include the prototypical t-butoxy carbonyl (t-BOC). Alternatively, a moiety such as cyanoalkyl acid is provided as a precursor to form the acid chloride of a reactant, perform the linkage with the second reactant, and thereafter reduce the cyano moiety to form the terminal amino group of an inventive conjugate. It is appreciated that other moieties are readily converted to an amine group subsequent to the conjugation chemistry. In a further example, carboxylprotective groups and the chemistry for the addition thereof are provided in *Protective Groups in Organic Synthesis* by T. W. Greene and P. G. M. Wuts, John Wiley & Sons, 1999. Carboxyl-protecting groups include, for example, groups such as methyl, ethyl, n-propyl, isopropyl, 1,1-dimethylpropyl, n-butyl, tert-butyl, and benzyl. It is further appreciated that side groups of amino acids included in a biologically active peptide may be protected as well.

In one embodiment of a process for forming an inventive conjugate, an ester moiety is formed, linking an EC and a peptide. In one example of this arrangement, the EC moiety $R_2$ includes a hydroxyl group which is reacted with a carboxyl group of the peptide, P, to form an ester linkage of EC and P. Illustratively, a condensation reaction is used to create an ester linkage of EC and P. For example, the endocannabinoid or derivative, or analog having a hydroxyl is reacted with a peptide having a carboxyl group in an organic solvent at a temperature in the range of about 20-100° C., for about 2-48 hours. A catalyst, such as dimethylaminopyridine, is optionally included in the reaction. Amino groups and reactive side groups present on the peptide are protected by addition of protective groups prior to the condensation reaction, as are other reactive side groups, as noted above. Protective groups are removed following formation of the ester linkage, for instance, under acidic conditions such as by treatment with 0.5N HCl.

In a further example, a transesterification reaction is performed in order to create an ester linkage of EC and P. For instance, the EC moiety $R_2$ having a hydroxyl group is modified by reaction with a lower alkyl alcohol $R_7$—OH forming $R_2$—O—$R_7$, where $R_7$ includes a lower alkyl group such as a methyl or ethyl group. The modified $R_2$ group having the form $R_2$—O—$R_7$ is included in a transesterification reaction with a peptide, P, to yield an inventive conjugate. In a particular transesterification example, the endocannabinoid component having a hydroxyl group, represented by the formula EC-OH, is reacted with methanol by combining these two reagents and reacting them at a temperature in the range of about 20-100° C., for about 1-48 hours to produce the modified reactant EC-O—$CH_3$. A catalyst, such as dimethylaminopyridine, is optionally included in the reaction. Further, the modified reactant EC-O—$CH_3$ and a peptide having a carboxyl group are combined in a reaction vessel along with an optional transesterification catalyst and incubated at a temperature in the range of about 20-250° C., for about 1-48 hours to produce an inventive conjugate EC-O—P and the byproduct $CH_3OH$. Amino groups and reactive side groups present on the peptide are protected by addition of protective groups prior to the transesterification reaction. Protective groups are removed, for instance, under acidic conditions such as by treatment with 0.5N HCl. Transesterification catalysts are known in the art and include titanium, antimony, lead, tin, manganese and zinc compounds, illustratively including alkyl titanates, lead phenolate, lead acetate, stannous octoate, tin(IV) oxide, dibutyltin oxide, dioctyltin oxide, dibutyltin dilaurate, dioctyltin dilaurate, butyltin hydroxide oxide, octyltin hydroxide, zinc acetate, zinc(IV) oxide, and zinc(II) oxide.

In another example of ester linkage formation, a peptide carboxyl group, preferably the C-terminal carboxyl is modified to an acyl chloride form and conjugated to EC in the presence of base to form the inventive conjugate EC-O—P. The acyl chloride form of the moiety C is formed for instance by incubation of C with a chloride compound such as thionyl chloride, phosphorus trichloride or phosphorus pentachloride.

The transport of endocannabinoids and derivative, or analogs thereof into cells and/or across the blood brain barrier has been described and an inventive conjugate is believed to likely provide a synergistic therapeutic effect, due, at least in part to increased transport of a biologically active peptide to a target cell when conjugated to an endocannabinoid or derivative, or analog thereof. In a particular embodiment, the bond between EC and P is hydrolyzable in a cell or organism. Thus, for example, an inventive conjugate is cleaved to yield an endocannabinoid EC and a peptide P in an organism or cell following delivery thereto. Alternatively, the bond is stable to hydrolysis or other cleavage and the conjugate provides the desired pharmacological effect without cleavage.

Optionally, a linker species is provided intermediate between the endocannabinoid or derivative, or analog EC and the biologically active peptide of an inventive conjugate compound. The linker in simplest form includes a moiety reactive with a terminal hydroxyl or amine group of EC as described herein, and a second moiety reactive with the biologically active peptide, particularly the N-terminal amine or C-terminal carboxyl group of the biologically active peptide. Substituents extending from a linker are provided to modify the lipophilicity of an inventive conjugate, or tether a dye or spectroscopic marker. With the inclusion of a linker, care should be taken to limit both the molecular weight and the hydrophilicity of the linker in order to retain the ability to traverse the blood brain barrier. Typically, the linker has eight or less backbone carbon atoms. Preferably, the linker backbone is linked to the cannabinoid agonist portion of an inventive conjugate through a carbon atom, an oxygen atom or a nitrogen atom. The linker moiety reactive with the moiety EC illustratively forms an amide and an ester linkage. Suitable chemistries for a variety of potential reaction moieties are found in Comprehensive Organic Transformations, R. C. Larock, John Wiley & Sons 1999.

It is appreciated that a linker, when present, is the preferred site for the attachment of an additional species. A substituent is optionally provided pendent from the linker backbone. The substituent illustratively includes a radioactive atom, a magnetic spectroscopically active marker and an organic dye. A radioactive atom is alternatively operative as a marker in isotope studies such as positron emission tomography, single photon emission computer tomography, radiological studies and the like. Common radio-isotopes used in medical imaging illustratively include 123I, $^{99m}$Tc, and other chelated radioisotopes as detailed in U.S. Pat. No. 6,241,963. Spectroscopically active markers include NMR/MRI active contrast enhancing moieties known to the art such as gadolinium, as detailed in Contrast Agents 1: Magnetic Resonance Imaging (Topics in Current Chemistry, 221) by Werner Krause, Springer Verlag, Berlin, Germany. Organic dyes, while recognized to have potentially distinct NMR signatures, are provided to yield an optically active spectroscopic signature suitable for biopsy, surgical identification, or preclinical studies of tissue treated by an inventive compound.

Pharmaceutical Compositions

The compounds of the present invention can be administered to a patient either alone or as part of a pharmaceutical composition. The inventive compositions are suitable for administration to patients by a variety of routes including intrathecally, intraventricularly, intravenously, orally, parenterally, and mucosally.

An inventive pharmaceutical composition includes a compound as described herein and a pharmaceutically acceptable carrier.

Compositions suitable for delivery illustratively include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers; diluents; solvents; or vehicles include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants.

Compositions suitable for injection optionally include physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and the like. Prolonged absorption of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, an inventive conjugate is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 5 associated with stomach acids, yet dissolves above pH 5 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particularly preferred enteric coating material for use herein are those acrylic acid polymers and copolymers available under the trade name EUDRAGIT®, Roehm Pharma (Germany). The EUDRAGIT® series L, L-30D and S copolymers are most preferred since these are insoluble in stomach and dissolve in the intestine.

The enteric coating provides for controlled release of the active agent, such that release is accomplished at a predictable location in the lower intestinal tract below the point at which drug release would occur absent the enteric coating. The enteric coating also prevents exposure of the active agent and carrier to the epithelial and mucosal tissue of the buccal cavity, pharynx, esophagus, and stomach, and to the enzymes associated with these tissues. The enteric coating therefore helps to protect the active agent and a patient's internal tissue from any adverse event prior to drug release at the desired site of delivery. Furthermore, the coated solid dosages of the present invention allow optimization of drug absorption, active agent protection, and safety. Multiple enteric coatings targeted to release the active agent at various regions in the lower gastrointestinal tract would enable even more effective and sustained improved delivery throughout the lower gastrointestinal tract.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6.sup.th Ed. (Media, PA: Williams & Wilkins, 1995).

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to an inventive conjugate, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

An inventive conjugate is optionally delivered in conjunction with an active therapeutic compound in one embodiment. A therapeutic compound suitable in this regard illustratively includes an antibiotic, a gamma or beta radiation emitting species, an anti-inflammatory, an antitumoral, an antiviral, an antibody, a hormone, an enzyme, and antigenic peptide or protein.

EXAMPLES

The examples presented below are intended to illustrate particular embodiments of the invention and are not intended to limit the scope of the specification, including the claims.

Example 1

Preparation of Virodhamyl-Leu Enkephalin Conjugate

A mixture of virodhamine (5 mmol) and t-butoxycarbonyl (t-Boc) amine-protected leu-enkephalin (5 mmol) is added to 0.1M carbodiimide [N-ethyl-N'-(3-dimethylaminopropyl) carbodiimide or EDC] in dimethylformamide (DMF), such that the final volume is 200 ml. The reaction is performed for 24 hours at 4° C. The resulting virodhamyl-leu enkephalin conjugate is collected and purified to pharmaceutical purity. Protecting groups are removed by treatment with trifluoroacetic acid (TFA): dichloromethane (DCM) (1:1) for 30 minutes at room temperature.

Example 2

Preparation of a Peptide Ester of Anandamide

An endocannabinoid, anandamide (5 mmol), is reacted with an excess of methanol to create an ester by combining the anandamide and methanol and reacting the reagents at a temperature of about 60° C., for about 24 hours to produce the modified reactant anandamide-O—$CH_3$ [$CH_3O$—$CH_2CH_2NHC({=}O)(CH_2)_2(CH_2CH{=}CH)_4(CH2)_4CH_3$]. A catalyst, such as dimethylaminopyridine, is optionally included in the reaction. The anandamide-O—$CH_3$ and t-butoxycarbonyl (t-Boc) amine-protected leu enkephalin (5 mmol) are combined in a reaction vessel along with an optional transesterification catalyst and incubated at a temperature in the range of about 80° C., for about 24 hours to produce an inventive conjugate (Tyr-Gly-Gly-Phe-$NH_2$—CH—(CH—$(CHD_2)C({=}O)0$—$CH_2CH_2NHC({=}O)(CH_2)_2(CH_2CH{=}CH)_4(CH2)_4CH_3$) and the byproduct $CH_3OH$. The conjugate is collected and purified to pharmaceutical purity. Protecting groups are removed by treatment with acid.

Any patents or publications mentioned in this specification are herein incorporated by reference to the same extent as if each individual publication was specifically and individually indicated to be incorporated by reference The compounds, compositions and processes described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

I claim:

1. A compound having the structure:

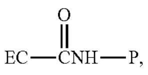 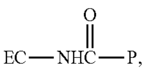 or 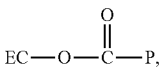

wherein P is a biologically active opioid peptide, and EC is an endocannabinoid bonded through a terminal moiety and prior to bonding EC has a structure of:

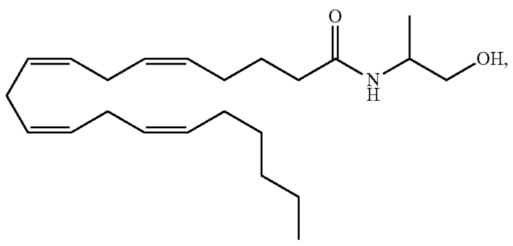

-continued
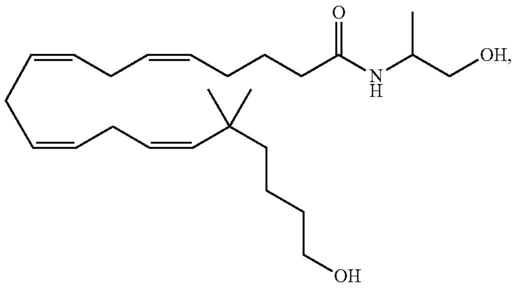
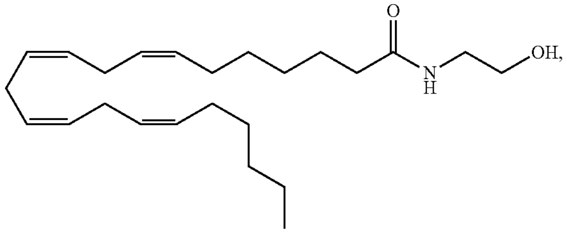
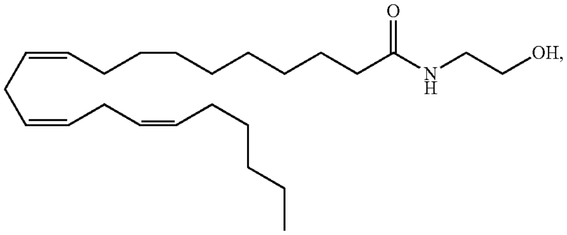
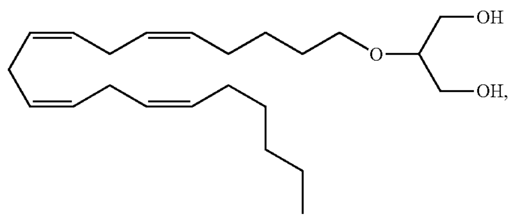
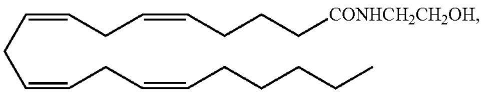
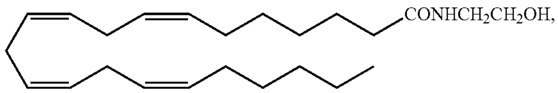
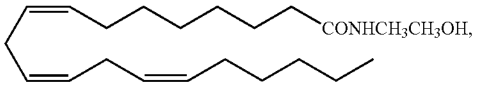
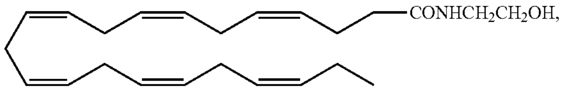
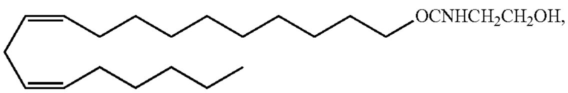
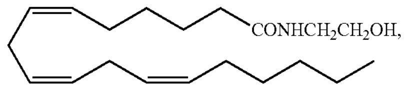
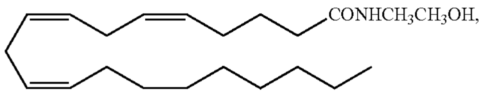
-continued
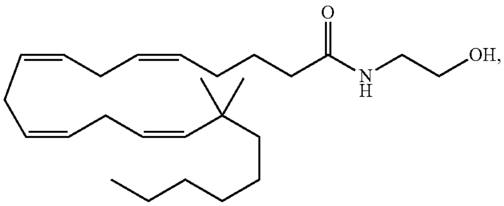
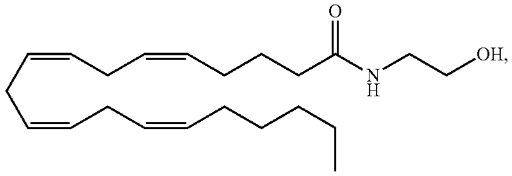
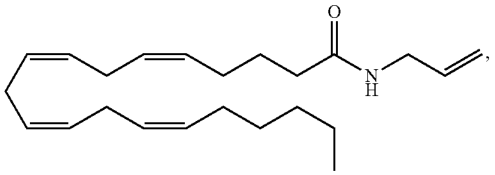
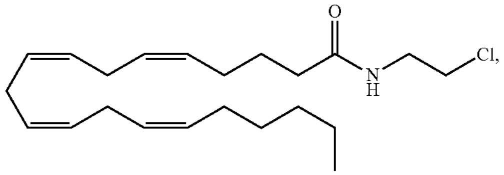
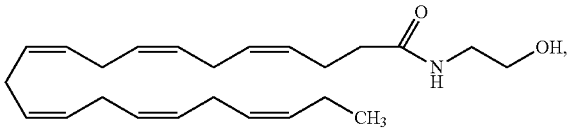
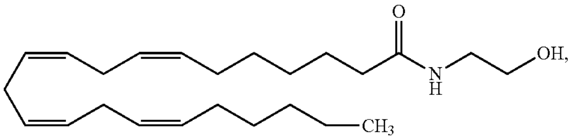
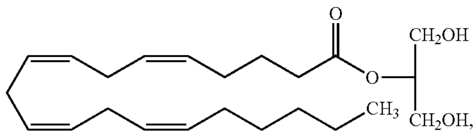
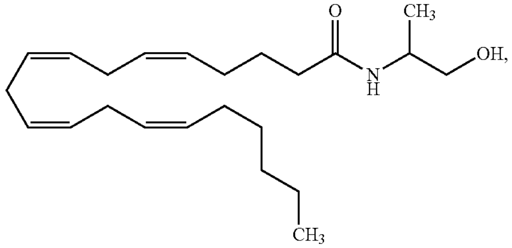
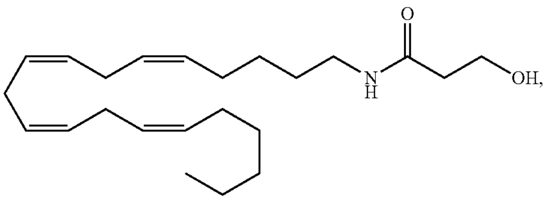
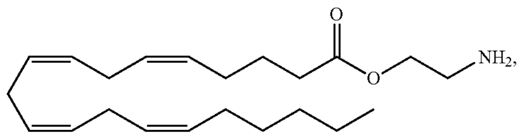

-continued

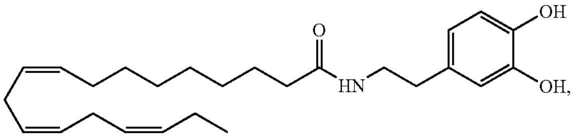

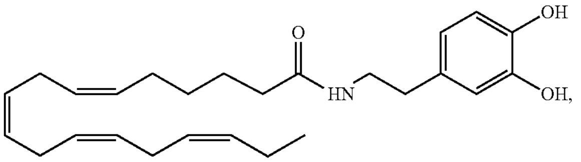

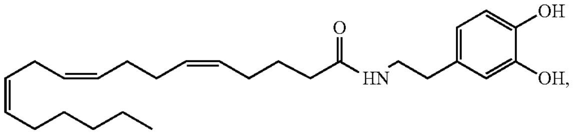

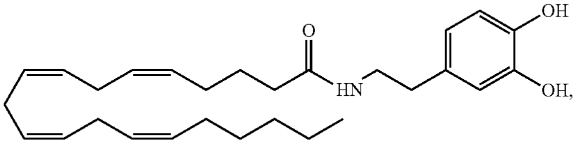

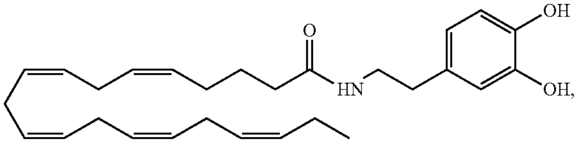

or

-continued

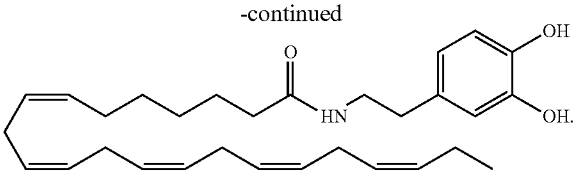

2. The compound of claim 1 wherein the opioid peptide is selected from the group consisting of: an enkephalin, an endorphin, an endomorphin and a dynorphin.

3. The compound of 1 wherein the opioid peptide is selected from the group consisting of: dermorphin, dermenkephalin, deltorphin I, deltorphin II, Leu enkephalin, Met enkephalin, dynorphin A, dynorphin B, alpha-neoendorphin, beta.-neoendorphin, metorphamide, beta-endorphin, DAMGO, DPDPE, DSLET , DADL, CTOP, FK-33824, morphiceptin, DALCE, endomorphin-1, endomorphin-2, beta.-casomorphin, DALDA, PL01, DAGO, hemorphin-4, CTP, CTAP, TAPS, MIF-1, Tyr-MIF-1, Tyr-W-MIF-1, Tyr-Pro-Trp and Tyr-Pro-Trp-Gly (SEQ ID NO: 33).

4. A pharmaceutical composition comprising:

a compound according to claim 1; and a pharmaceutically acceptable carrier.

5. The compound of claim 1 having the structure:

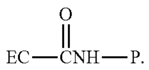

* * * * *

SEQUENCE LISTING

```
<160> NUMBER OF SEQ ID NOS: 33

<210> SEQ ID NO 1
<211> LENGTH: 7
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Dermorphin connected to endocannibinoid
      Ala is D amino acid alanine

<400> SEQUENCE: 1

Tyr Ala Phe Gly Tyr Pro Ser
1               5


<210> SEQ ID NO 2
<211> LENGTH: 7
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
```

<223> OTHER INFORMATION: Xaa is D amino acid methionine
<220> FEATURE:
<221> NAME/KEY: BINDING
<222> LOCATION: (6)..(6)
<223> OTHER INFORMATION: Dermenkephalin connected to endocannibinoid

<400> SEQUENCE: 2

Tyr Xaa Phe His Leu Met Asp
1 5

<210> SEQ ID NO 3
<211> LENGTH: 7
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Deltorphin I connected to endocannibinoid
<220> FEATURE:
<221> NAME/KEY: SITE
<222> LOCATION: (2)..(2)
<223> OTHER INFORMATION: Xaa is D amino acid alanine

<400> SEQUENCE: 3

Tyr Xaa Phe Asp Val Val Gly
1 5

<210> SEQ ID NO 4
<211> LENGTH: 7
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Deltorphin II connected to endocannibinoid

<400> SEQUENCE: 4

Tyr Ala Phe Glu Val Val Gly
1 5

<210> SEQ ID NO 5
<211> LENGTH: 5
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (5)..(5)
<223> OTHER INFORMATION: Enkephalin connected to endocannibinoid

<400> SEQUENCE: 5

Tyr Gly Gly Phe Leu
1 5

<210> SEQ ID NO 6
<211> LENGTH: 5
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (5)..(5)
<223> OTHER INFORMATION: Enkephalin connected to endocannibinoid

<400> SEQUENCE: 6

-continued

Tyr Gly Gly Phe Met
1 5

<210> SEQ ID NO 7
<211> LENGTH: 17
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Dynorphin A connected to endocannibinoid

<400> SEQUENCE: 7

Tyr Gly Gly Phe Leu Arg Arg Ile Arg Pro Lys Leu Lys Trp Asp Asn
1 5 10 15

Gln

<210> SEQ ID NO 8
<211> LENGTH: 13
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Dynorphin B connected to endocannabinoid

<400> SEQUENCE: 8

Tyr Gly Gly Phe Leu Arg Arg Gln Phe Lys Val Val Thr
1 5 10

<210> SEQ ID NO 9
<211> LENGTH: 10
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Alpha-neoendorphin connected to endocannibinoid

<400> SEQUENCE: 9

Tyr Gly Gly Phe Leu Arg Lys Tyr Pro Lys
1 5 10

<210> SEQ ID NO 10
<211> LENGTH: 9
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Beta-neoendorphin connected to endocannibinoid

<400> SEQUENCE: 10

Tyr Gly Gly Phe Leu Arg Lys Tyr Pro
1 5

<210> SEQ ID NO 11
<211> LENGTH: 8
<212> TYPE: PRT
<213> ORGANISM: Artificial Sequence
<220> FEATURE:
<223> OTHER INFORMATION: synthesized sequence

```
<220> FEATURE:
<221> NAME/KEY: BINDING
<222> LOCATION: (2)..(2)
<223> OTHER INFORMATION: Metorphamide connected to endocannibinoid

<400> SEQUENCE: 11

Tyr Gly Gly Phe Met Arg Arg Val
1               5


<210> SEQ ID NO 12
<211> LENGTH: 31
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Beta-endorphin connected to endocannibinoid

<400> SEQUENCE: 12

Tyr Gly Gly Phe Met Thr Ser Glu Lys Ser Gln Thr Pro Leu Val Thr
1               5                   10                  15

Leu Phe Lys Asn Ala Ile Ile Lys Asn Ala Tyr Lys Lys Gly Glu
            20                  25                  30


<210> SEQ ID NO 13
<211> LENGTH: 6
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Enkephalin connected to
      endocannibinoid
<220> FEATURE:
<221> NAME/KEY: SITE
<222> LOCATION: (2)..(2)
<223> OTHER INFORMATION: Xaa is D amino acid alanine
<220> FEATURE:
<221> NAME/KEY: SITE
<222> LOCATION: (4)..(4)
<223> OTHER INFORMATION: Xaa is methyl phenylalanine
<220> FEATURE:
<221> NAME/KEY: SITE
<222> LOCATION: (5)..(5)
<223> OTHER INFORMATION: Xaa is hydroxylated glycine

<400> SEQUENCE: 13

Tyr Xaa Gly Xaa Xaa Lys
1               5


<210> SEQ ID NO 14
<211> LENGTH: 6
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D-pen penicillanine (3-mercaptovaline)
<220> FEATURE:
<221> NAME/KEY: SITE
<222> LOCATION: (5)..(5)
<223> OTHER INFORMATION: Xaa is D-pen penicillanine (3-mercaptovaline)

<400> SEQUENCE: 14

Tyr Xaa Gly Phe Xaa Lys
1               5
```

-continued

<210> SEQ ID NO 15
<211> LENGTH: 6
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D-amino acid alanine
<220> FEATURE:
<221> NAME/KEY: SITE
<222> LOCATION: (5)..(5)
<223> OTHER INFORMATION: Xaa is D-amino acid serine

<400> SEQUENCE: 15

Tyr Xaa Gly Phe Xaa Thr
1 5

<210> SEQ ID NO 16
<211> LENGTH: 6
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D amino acid alanine
<220> FEATURE:
<221> NAME/KEY: SITE
<222> LOCATION: (5)..(5)
<223> OTHER INFORMATION: Xaa is D amino acid leucine

<400> SEQUENCE: 16

Tyr Xaa Gly Phe Xaa Lys
1 5

<210> SEQ ID NO 17
<211> LENGTH: 8
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (1)..(1)
<223> OTHER INFORMATION: Xaa is D-amino acid Phenylalanine
<220> FEATURE:
<221> NAME/KEY: SITE
<222> LOCATION: (4)..(4)
<223> OTHER INFORMATION: Xaa is D-amino acid tryptophan
<220> FEATURE:
<221> NAME/KEY: SITE
<222> LOCATION: (5)..(5)
<223> OTHER INFORMATION: Xaa is ornithine
<220> FEATURE:
<221> NAME/KEY: SITE
<222> LOCATION: (7)..(7)
<223> OTHER INFORMATION: Xaa is penicillamine (3-mercaptovaline)

<400> SEQUENCE: 17

Xaa Cys Tyr Xaa Xaa Thr Xaa Thr
1 5

<210> SEQ ID NO 18
<211> LENGTH: 6
<212> TYPE: PRT
<213> ORGANISM: Artificial Sequence
<220> FEATURE:
<223> OTHER INFORMATION: synthesized sequence
<220> FEATURE:

-continued

<221> NAME/KEY: SITE
<222> LOCATION: (4)..(4)
<223> OTHER INFORMATION: Xaa is methyl phenylalanine
<220> FEATURE:
<221> NAME/KEY: SITE
<222> LOCATION: (5)..(5)
<223> OTHER INFORMATION: Xaa is hydroxylated methionine

<400> SEQUENCE: 18

Tyr Ala Gly Xaa Xaa Lys
1 5

<210> SEQ ID NO 19
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (4)..(4)
<223> OTHER INFORMATION: Morphiceptin connected to endocannibinoid

<400> SEQUENCE: 19

Tyr Pro Phe Pro
1

<210> SEQ ID NO 20
<211> LENGTH: 6
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D amino acid alanine

<400> SEQUENCE: 20

Tyr Xaa Gly Phe Leu Cys
1 5

<210> SEQ ID NO 21
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (4)..(4)
<223> OTHER INFORMATION: Endomorphin-1 connected to endocannibinoid

<400> SEQUENCE: 21

Tyr Pro Trp Phe
1

<210> SEQ ID NO 22
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (4)..(4)
<223> OTHER INFORMATION: Endomorphin-2 connected to endocannibinoid

<400> SEQUENCE: 22

Tyr Pro Phe Phe
1

<210> SEQ ID NO 23
<211> LENGTH: 7
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (4)..(4)
<223> OTHER INFORMATION: Beta-casomorphin connected to endocannibinoid

<400> SEQUENCE: 23

Tyr Pro Phe Val Glu Pro Ile
1               5

<210> SEQ ID NO 24
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D-amino acid arginine

<400> SEQUENCE: 24

Tyr Xaa Phe Lys
1

<210> SEQ ID NO 25
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (3)..(3)
<223> OTHER INFORMATION: Xaa is N-methylated phenylalanine
<220> FEATURE:
<221> NAME/KEY: SITE
<222> LOCATION: (4)..(4)
<223> OTHER INFORMATION: Xaa is D amino acid proline

<400> SEQUENCE: 25

Tyr Pro Xaa Xaa
1

<210> SEQ ID NO 26
<211> LENGTH: 5
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D amino acid alanine
<220> FEATURE:
<221> NAME/KEY: SITE
<222> LOCATION: (4)..(4)
<223> OTHER INFORMATION: Xaa is N-methylated phenylalanine
<220> FEATURE:
<221> NAME/KEY: SITE
<222> LOCATION: (5)..(5)
<223> OTHER INFORMATION: Xaa is hydroxylated glycine

<400> SEQUENCE: 26

Tyr Xaa Gly Xaa Xaa
1               5

<210> SEQ ID NO 27
<211> LENGTH: 6
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D amino acid serine

<400> SEQUENCE: 27

Tyr Xaa Gly Phe Leu Thr
1               5

<210> SEQ ID NO 28
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (2)..(2)
<223> OTHER INFORMATION: Hemorphin-4 connected to endocannibinoid

<400> SEQUENCE: 28

Tyr Pro Trp Thr
1

<210> SEQ ID NO 29
<211> LENGTH: 8
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (1)..(1)
<223> OTHER INFORMATION: Xaa is D amino acid phenylalanine
<220> FEATURE:
<221> NAME/KEY: SITE
<222> LOCATION: (4)..(4)
<223> OTHER INFORMATION: Xaa is D amino acid tryptophan
<220> FEATURE:
<221> NAME/KEY: SITE
<222> LOCATION: (7)..(7)
<223> OTHER INFORMATION: Xaa is penicillamine (3-mercaptovaline)

<400> SEQUENCE: 29

Xaa Cys Tyr Xaa Lys Thr Xaa Thr
1               5

<210> SEQ ID NO 30
<211> LENGTH: 8
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (4)..(4)
<223> OTHER INFORMATION: Xaa is D amino acid tryptophan
<220> FEATURE:
<221> NAME/KEY: SITE
<222> LOCATION: (7)..(7)
<223> OTHER INFORMATION: Xaa is pencillamine (3-mercaptovaline)

-continued

```
<400> SEQUENCE: 30

Phe Cys Tyr Xaa Arg Thr Xaa Thr
1               5


<210> SEQ ID NO 31
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: SITE
<222> LOCATION: (2)..(2)
<223> OTHER INFORMATION: Xaa is D amino acid arginine
<220> FEATURE:
<221> NAME/KEY: SITE
<222> LOCATION: (4)..(4)
<223> OTHER INFORMATION: Xaa is sacrosine (N-methylglycine)

<400> SEQUENCE: 31

Tyr Xaa Phe Xaa
1


<210> SEQ ID NO 32
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (4)..(4)
<223> OTHER INFORMATION: Tyr-MIF-1 connected to endocannibinoid

<400> SEQUENCE: 32

Tyr Pro Leu Gly
1


<210> SEQ ID NO 33
<211> LENGTH: 4
<212> TYPE: PRT
<213> ORGANISM: Artificial Sequence
<220> FEATURE:
<223> OTHER INFORMATION: synthesized sequence
<220> FEATURE:
<221> NAME/KEY: BINDING
<222> LOCATION: (4)..(4)
<223> OTHER INFORMATION: Tyr-W-MIF-1 connected to endocannibinoid

<400> SEQUENCE: 33

Tyr Pro Trp Gly
1
```